United States Patent
Peemans et al.

(12)

(10) Patent No.: US 6,245,951 B1
(45) Date of Patent: Jun. 12, 2001

(54) PROCESS FOR CLEANING BISPHENOL PRE-REACTOR

(75) Inventors: Rudy Peemans, Erps-Kwerps (BE); Jan-Peter Visser, Numansdorp (NL); Hendrik Herman Caré, Steenbergen (NL); Edwin Van Der Schuit, Ossendrecht (NL); Robbert Vos, Bergen op (NL)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/416,097

(22) Filed: Oct. 12, 1999

(51) Int. Cl.[7] .................................................. C07C 39/16
(52) U.S. Cl. ............................................. 568/728; 568/727
(58) Field of Search ...................................... 568/727, 728

(56) References Cited

U.S. PATENT DOCUMENTS

| 4,107,218 | 8/1978 | Konrad et al. . |
| 4,294,994 | 10/1981 | Li . |
| 5,210,329 | 5/1993 | Gomes de Matos et al. . |
| 5,243,093 | 9/1993 | Kissinger et al. . |
| 5,245,088 | 9/1993 | Fimuro et al. . |
| 5,288,926 | 2/1994 | Patrascu et al. . |
| 5,368,827 | 11/1994 | Moriya et al. . |
| 5,786,522 | 7/1998 | Cipullo . |
| 5,874,644 | 2/1999 | Gammill . |

FOREIGN PATENT DOCUMENTS

| 197 57 570 | 6/1999 | (DE) . |
| 0 323 831 | 7/1989 | (EP) . |

*Primary Examiner*—Michael L. Shippen
(74) *Attorney, Agent, or Firm*—Oppedahl & Larson LLP

(57) ABSTRACT

In a semicontinuous method for manufacturing bisphenols, reduced fouling in the pre-reactor is achieved by using two or more prereactors are used to continuously condense the dihydric phenol and the ketone or aldehyde to produce a partial reaction product in which the reaction of the dihydric phenol and the ketone or aldehyde is 10 to 70% complete. This partial reaction product is continuously removed from the pre-reactors, combined and introduced to a batchwise completion reactor. A stream of water or aqueous hydrochloric acid is added in alternating intervals to the pre-reactors, such that one is being cleaned by shifting the solubility of the bisphenol product at the same time that the other(s) continue to product a normal product stream which includes seed crystals for enhancing the performance of the batchwise completion reactor.

8 Claims, 2 Drawing Sheets

PROCESS FOR CLEANING BISPHENOL PRE-REACTOR

FIELD OF THE INVENTION

This application relates to a process for reducing fouling of cooling surfaces of pre-reactors used in the production of bisphenols, such as bisphenol A.

BACKGROUND OF THE INVENTION

Bisphenols, and in particular bisphenol A (2,2 bis(p-hydroxyphenyl) propane, "BPA"), have become industrially significant reactants for a number of processes including the preparation of polycarbonates. Bisphenols are prepared on an industrial scale by one of two processes: an acid-catalyzed or HCl process and an ion exchange process, in which an acidic ion exchange resin such as sulfonic acid-substituted polystyrene is employed.

The bisphenol is prepared by condensation of two moles of phenol with one mole of a ketone or aldehyde, for example acetone, in the presence of an acidic catalyst. In addition to the bisphenol, however, the product stream from the reaction includes unreacted phenol, which is included in excess over the stoichiometric requirement, and various isomers of the desired bisphenol and other by-products. Because these by-products can compromise the properties of products made using the bisphenol, they need to be separated. One technique for accomplishing this separation involves cooling the product stream to induce crystallization of a 1:1 bisphenol:phenol adduct which can then be further processed by washing, distillation, extraction and/or steam stripping to produce a purified bisphenol product. Processes for the production and purification of bisphenols are well known, and are described inter alia in U.S. Pat. Nos. 4,107,218; 4,294,994; 5,210,329; 5,243,093; 5,245,088; 5,288,926; 5,368,827; 5,786,522; and 5,874,644.

In some semicontinuous procedures for the preparation of bisphenols, phenol and acetone are mixed and partially reacted in a pre-reactor. The partial reaction is allowed to proceed through 10 to 70% conversion, and the resulting product is then transferred to a batch reaction in which full conversion of the starting materials is achieved. The temperature in the pre-reactor is selected so that a little, BPA is precipitated. These crystals serve as seed crystals in the batch reactor. However, crystallization of BPA tends also to form a layer on interior surface of the pre-reactor, particularly the cooling surfaces which are used to maintain the temperature in the pre-reactor. This layer hinders heat transfer between these cooling surfaces and the reaction mixture. This reduced heat transfer can cause lower production rates and/or reduced purity of the finished product and is therefore undesirable.

To prevent these side effects, it is conventional to clean the pre-reactor periodically. This is done by either filling the pure phenol or with a normal charge where extra water or acid is added. These procedures increases the solubility of BPA and the removal of the BPA layer from the cooling surfaces, but the product produced during these cleaning procedures does not meet product specification. Thus, the time spent cleaning is wasted from a productivity point-of-view, and there is a need for an improved method for manufacture of bisphenols, in which this disruption is reduced or eliminated.

SUMMARY OF THE INVENTION

The present invention provides a semicontinuous method for manufacturing bisphenols with reduced fouling in the pre-reactor. In accordance with this method, two or more prereactors are used to continuously condense the dihydric phenol and the ketone or aldehyde to produce a partial reaction product in which the reaction of the dihydric phenol and the ketone or aldehyde is 10 to 70% complete. This partial reaction product is continuously removed from the pre-reactors, combined and introduced to a batchwise completion reactor. A stream of water or aqueous hydrochloric acid is added in alternating intervals to the pre-reactors, such that one is being cleaned by shifting the solubility of the bisphenol product at the same time that the other(s) continue to product a normal product stream which includes seed crystals for enhancing the performance of the batchwise completion reactor.

DETAILED DESCRIPTION OF THE INVENTION

Figure 1:
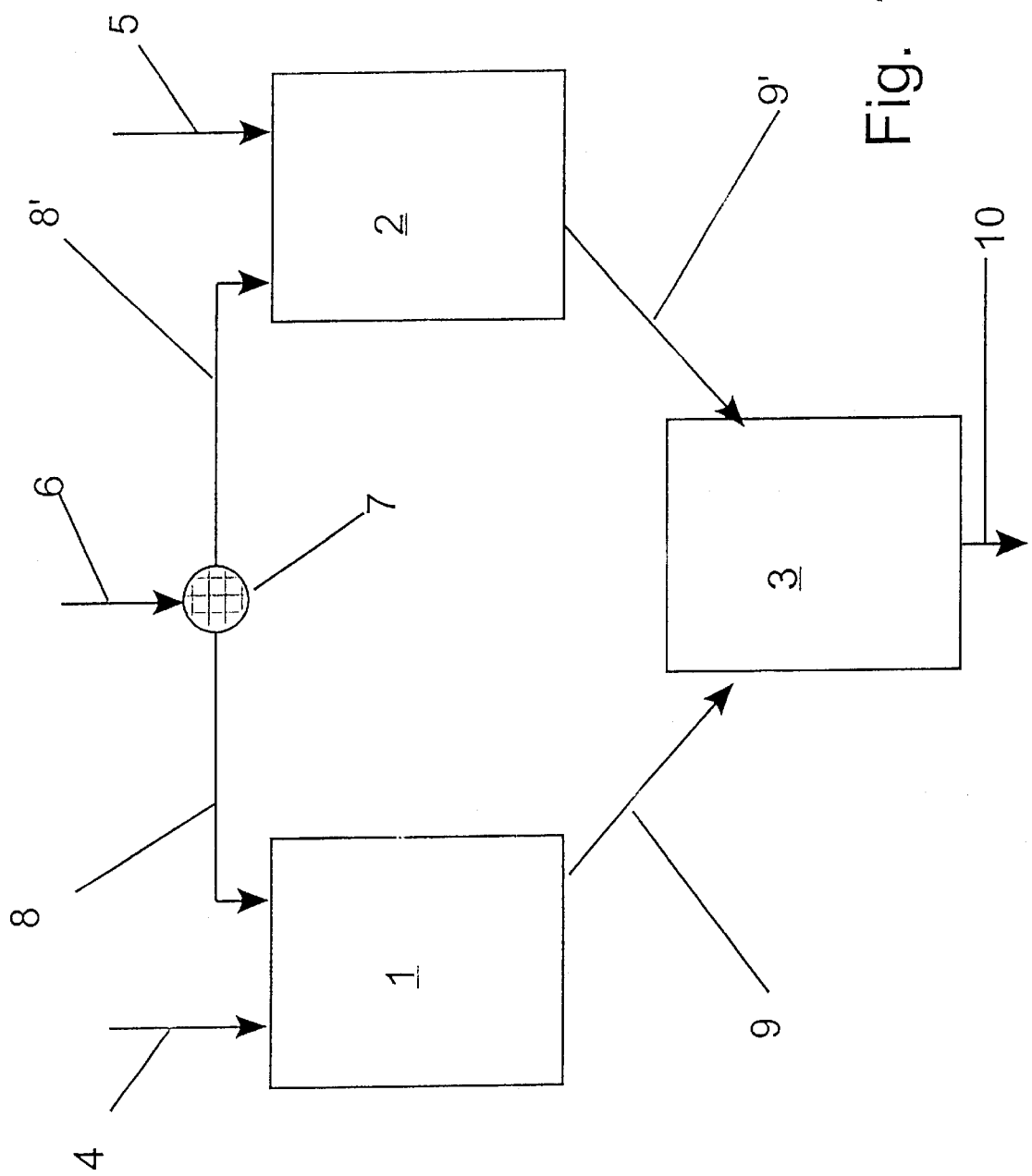
FIG. 1 shows a schematic representation of an apparatus for performing the method of the invention.

FIG. 1 shows a schematic representation of a basic apparatus for performing the method of the invention. The apparatus comprises two pre-reactors 1 and 2, and a batch completion reactor 3. Reactants (for example, phenol and acetone) are introduced to pre-reactors 1 and 2 via lines 4 and 5, respectively. Line 6 supplies water or aqueous HCl to valve 7 which controls the supply of water of aqueous HCl to pre-reactors 1 and 2 via lines 8 and 8', respectively. Product from the pre-reactors 1 and 2 is transferred to the batch completion reactor 3 via lines 9 and 9'. Completed product is removed from the batch completion reactor via line 10.

Figure 2:
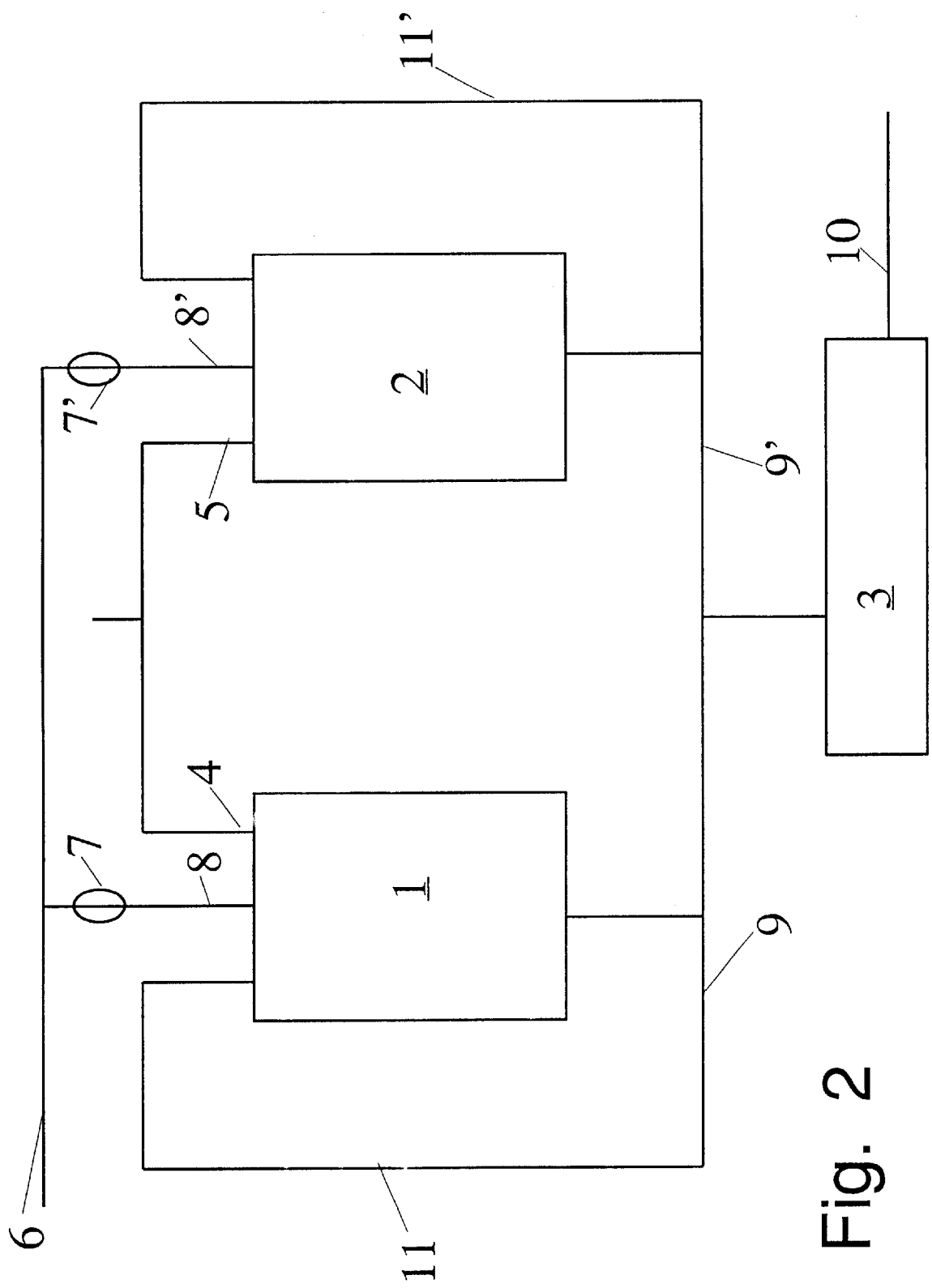
FIG. 2 shows a schematic representation of an alternative apparatus for performing the method of the invention.

FIG. 2 shows a more sophisticated apparatus for practicing the method of the invention. In this case, line 6 supplying water or aqueous HCl to the pre-reactors is split, and separate valves 7 and 7' are provided to control the flow into pre-reactors 1 and 2, respectively. In addition, product withdrawn from the pre-reactors may be recycled via lines 11 and 11' rather than being directed exclusively to batch completion reactor 3. In addition, lines 9 and 9' are combined prior to the batch completion reactor 3. Interchange of materials between the first and second pre-reactors 1 and 2 may also be provided if desired, either via the lines shown or through additional lines. Such interchange can be used to speed the recovery to normal operating conditions in a pre-reactor following cleaning, or to accelerate the start of the cleaning cycle.

In operation, valve 7 or valves 7 and 7' are used to control the input of water of aqueous HCl to the pre-reactors 1 and 2. The valve is operated so that one pre-reactor at a time is receiving an input flow of water and HCl, i.e., so that water or aqueous hydrochloric acid is added in alternating intervals to the pre-reactors 1 and 2. The time interval can be empirically optimized for a given size of pre-reactor and set of operating conditions. In general, a schedule in which the flow of water or aqueous HCl is shifted from one reactor to another every 2 to 48 hours, and preferably about every 24 hours, is sufficient to reduce fouling of the pre-reactor while maintaining production of good quality product. During the time period when the flow of water of aqueous HCl is being supplied to a given pre-reactor, it is not necessary that the flow be constant. Thus, for example, in one embodiment of the invention it was found effective to maintain a cycle of a first flow rate for two hours, followed by a double flow rate for one hour. Since the higher flow rate will lead to increased dissolution of crystallized bisphenol but a decrease in seed crystals available to the batch completion reactor, flow variation to the pre-reactor can be used to fine tune the operation to produce the best quality product with the least amount of fouling.

The rate at which water or aqueous HCl is introduced into the pre-reactors cannot meaningfully be expressed as a specific number, because the desired amount is dependent on various factors including the volume of the pre-reactor, the concentration of HCl, if present, and the rate at which reactants are supplied. In general, it is desirable to tune the feed rate to achieve a balance of cleaning activity and product quality. For example, in one embodiment of the invention using a pre-reactor with a reactant feed rate of 9 to 14 m$^3$/hour, the feed rate of water of aqueous HCl is in the range of 0 to 360 kg/hr, preferably 75 to 250 kg/hr.

Although water alone can be used in the method of the invention, better results are achieved if aqueous HCl is utilized instead. In embodiments employing HCI, the stream is suitably 1.3 to 63 wt % HCl (as a 33% solution). Of course, it will be appreciated that a single stream with a suitable concentration of HCl can be prepared in advance of introduction to the pre-reactors or that two streams, one of water and one of a more concentrated HCl can be combined in the pre-reactor to achieve the same result, and that such variations do not depart from the present invention.

Other variations in the method of practicing the invention may also be made. For example, depending on the relative capacities of the pre-reactors and the batch completion reactor, more than one batch completion reactor can be supplied by a set of pre-reactors. Similarly, while the invention is described above and illustrated using two pre-reactors, more than two pre-reactors could be used. In this case, the flow of water or aqueous HCl would be cycled among each of the pre-reactors in a manner selected to provide the desired product and performance characteristics.

Example 1

A plant having the general configuration shown in FIG. 1 was operated with an aqueous HCl solution (34%) being added to the pre-reactors 1 and 2 at alternating 24 hour time intervals. During each interval where the HCl solution was added, the flow rate was cycled on a schedule of two hours at 75 kg/hr and 1 hour at an increased flow rate of 250 kg/hr. Constant quality of product was maintained through 60 days, and the plant throughput increased 10% as compared to period descaling of the pre-reactors. Special descaling operations in which the line was taken down for a period of time were reduced from once every three days to about once per month.

What is claimed is:

1. A semicontinuous method for production of bisphenols by condensation of a dihydric phenol and a ketone or aldehyde comprising the steps of:

(a) continuously condensing the dihydric phenol and the ketone or aldehyde in a first pre-reactor to produce a partial reaction product in which the reaction of the dihydric phenol and the ketone or aldehyde is 10 to 70% complete;

(b) continuously condensing the dihydric phenol and the ketone or aldehyde in a second pre-reactor to produce a partial reaction product in which the reaction of the dihydric phenol and the ketone or aldehyde is 10 to 70% complete; and (c) continuously removing partial reaction product from the first and second pre-reactors and introducing the removed partial reaction product to a batchwise completion reactor, wherein a stream of water or aqueous hydrochloric acid is added in alternating intervals to the first and second pre-reactors.

2. The method of claim 1, wherein the stream of water or aqueous hydrochloric acid is added to the first pre-reactor for a period of from 2 to 48hours, and then to the second pre-reactor for a period of 2 to 48hours.

3. The method of claim 2, wherein rate at which the water or aqueous hydrochloric acid is added is varied between a low flow rate and a high flow rate during the period of addition to the first and/or second pre-reactor.

4. The method of claim 3, wherein the high flow rate is twice the low flow rate.

5. The method of claim 4, wherein the addition of water of aqueous hydrochloric acid is varied in a cyclic pattern of 2 hours at the low flow rate and 1 hour at the high flow rate.

6. The method of claim 3, wherein the addition of water of aqueous hydrochloric acid is varied in a cyclic pattern of 2 hours at the low flow rate and 1 hour at the high flow rate.

7. The method of claim 1, wherein aqueous HCl is added to the first and second pre-reactors, and the aqueous HCl has a concentration of 1.3 to 63 wt % HCl (as a 33% solution).

8. The method of claim 1, wherein the partial reaction products from the first and second pre-reactors are combined prior to introduction into the batch completion reactor.

* * * * *